US006869434B2

(12) United States Patent
Choi

(10) Patent No.: US 6,869,434 B2
(45) Date of Patent: Mar. 22, 2005

(54) ALIGNMENT SYSTEM FOR BONE FIXATION

(76) Inventor: Soon C. Choi, 86 Old Smalleytown Rd., Warren, NJ (US) 07059

(*) Notice: Subject to any disclaimer, the term of this patent is extended or adjusted under 35 U.S.C. 154(b) by 0 days.

(21) Appl. No.: 10/141,110

(22) Filed: May 8, 2002

(65) Prior Publication Data

US 2003/0212405 A1 Nov. 13, 2003

(51) Int. Cl.[7] .......................... A61B 17/90; A61B 17/78; A61B 17/56
(52) U.S. Cl. ............................. 606/97; 606/96; 606/98; 606/64
(58) Field of Search .................. 606/96–98, 65–68, 606/89, 80

(56) References Cited

U.S. PATENT DOCUMENTS

| | | | | | |
|---|---|---|---|---|---|
| 2,235,419 | A | * | 3/1941 | Callahan et al. | 606/96 |
| 2,531,734 | A | * | 11/1950 | Hopkins | 606/97 |
| 3,704,707 | A | * | 12/1972 | Halloran | 606/97 |
| 4,860,735 | A | * | 8/1989 | Davey et al. | 606/96 |
| 4,911,153 | A | * | 3/1990 | Border | 606/98 |
| 5,176,681 | A | * | 1/1993 | Lawes et al. | 606/98 |
| 5,295,991 | A | * | 3/1994 | Frigg | 606/62 |
| 5,352,228 | A | * | 10/1994 | Kummer et al. | 606/98 |
| 6,214,013 | B1 | * | 4/2001 | Lambrecht et al. | 606/96 |

* cited by examiner

Primary Examiner—David O. Reip
Assistant Examiner—Sarah Webb
(74) Attorney, Agent, or Firm—Henry I. Schanzer

(57) ABSTRACT

An alignment guide for setting the position and depth of a guide pin to be inserted into a bone. The alignment guide includes a mechanical assembly for deploying a calibrated guide rod along a selected external surface of the bone and for adjusting the guide rod so it lies parallel to a desired path extending through the bone for a selected distance. The position and orientation of the guide rod may be adjusted using imaging means for viewing the location of the desired path extending through the bone parallel to the guide rod. The alignment guide is mechanically linked to apparatus for subsequently inserting a guide pin into the bone parallel to the guide rod. In one embodiment the alignment guide is designed to aid a surgeon in centering the guide pin to be inserted in the femoral head and neck without repeated trial-and-error drilling. This shortens the operation time and reduces the radiation due to prolonged exposure to fluoroscopic equipment and reduces the risk of possible complications from the surgery.

17 Claims, 7 Drawing Sheets

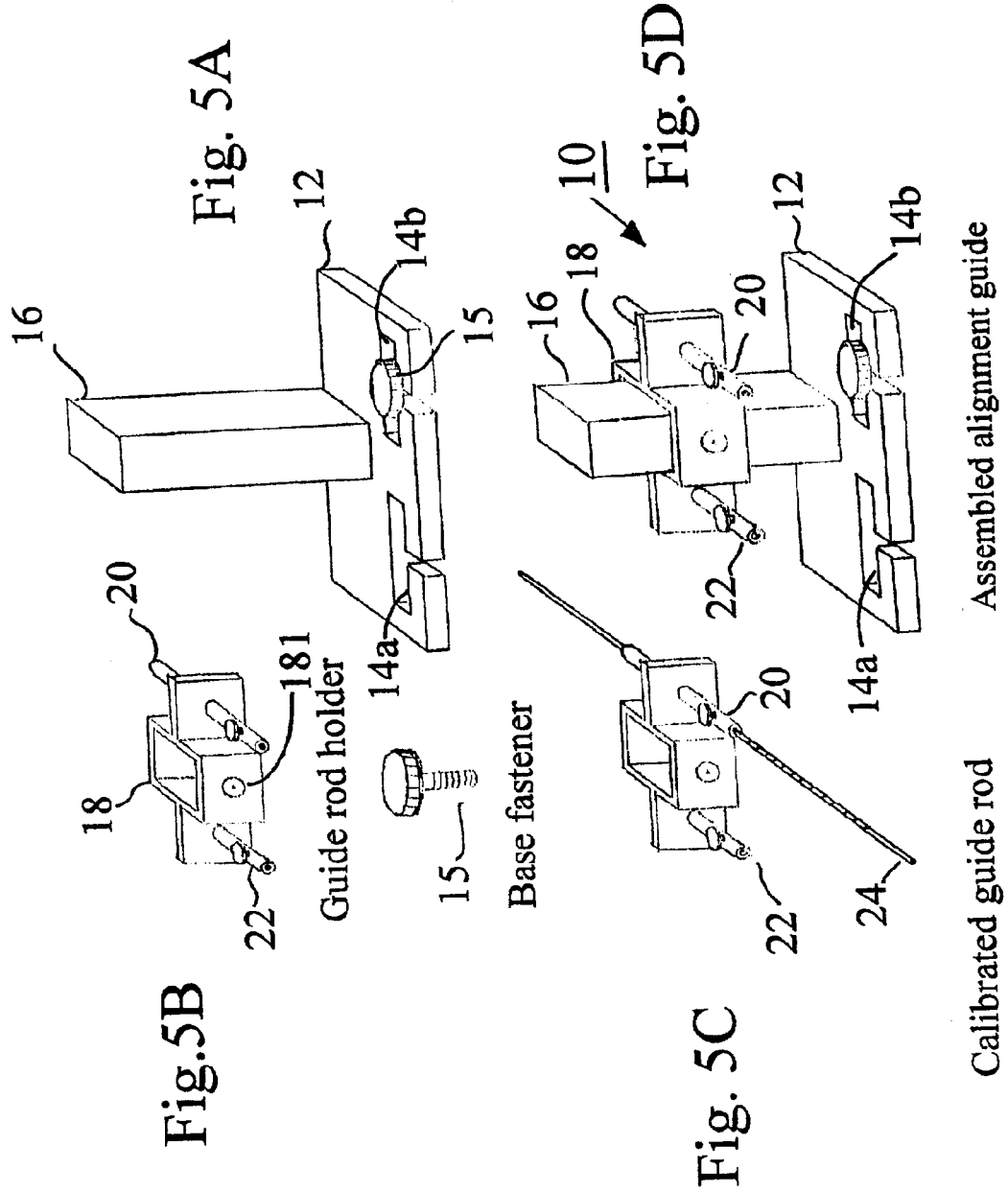

ALIGNMENT SYSTEM FOR BONE FIXATION

BACKGROUND OF INVENTION

This invention relates to apparatus and methods for more precisely aligning guide rods and guide pins into bones for bone fixation.

To better understand the problem faced by the inventor and resolved by the invention reference will first be made to the prior art shown in FIGS. 1–4.

Currently available femoral nail systems for the fixation of femoral or certain types of hip fracture and the prophylactic fixation of pending hip or femoral fracture have been described in several trade publications including: (a) The Titanium Femoral Nail System (Synthes); (b) TRIGEN® IM Nail System (Smith+Nephew, Inc.); (c) Intramedullary Hip Screw Nail (Smith+Nephew, Inc.); (d) M/DN® Intramedullary Fixation (Zimmer, Bristol Myers Squibb Co.); (e) AIM® Titanium Femoral Nail System (DePuy ACE, Johnson & Johnson Co); (f) GAMMA Locking Nail (Howmedica); and (g) UNIFLEX Nailing System (BIOMET). These known systems have design features, as shown in FIGS. 1A, 1B, and 1C, which allow insertion of metal rods (e.g., 102), also referred to herein as an intramedullary nail (IM nail), into the medullary canal of the femur (e.g., 104) and insertion of additional lag screws (e.g., 106) or blades (e.g., 108) through slots in the intramedullary nail (IM nail), 102, into the femoral head (110) and neck (112) for additional stability of fracture fixation. FIG. 1A shows the use of two lag screws in the femoral head. FIGS. 1B and 1C show the use of a single blade 108 or screw 106 along the center line of the femoral head and neck. As shown in FIG. 2, known fixation systems include a device commonly called a drill guide, a targeting device, or aiming arm (120) attached to the top end of the IM nail to ensure the correct insertion of lag screws (106) or blades (108) through slots in the IM nail.

Correct positioning of the IM nail 102 is critical to ensure the lag screws or blades are placed in the center of the femoral head 110 and neck 112 in both anteroposterior (AP) and lateral planes for the single screw or blade. For the two screw system as shown in FIG. 1A, the IM nail 102 must also be positioned to cause the two screws to be placed parallel to each other in the AP view and in the center of the femoral head and neck in the lateral view. However, no device or guide is available at this time to aid in the correct placement of lag screws or blades in the center of the femoral head and neck. As shown in the cross-sectional diagram of FIG. 3 (AP view), since the depth of the IM nail 102 is not exactly defined relative to the femoral head and neck, a guide pin 130 driven by means of guide 120 (see FIG. 2) into the femoral head may be too high (position A) or too low (position B), rather than being in the correct center position C. Likewise, as shown in the top (lateral) view of FIG. 4, since the rotation of the IM nail 102 is not exactly defined relative to the femoral head and neck, a guide pin 130 driven via the drill guide 120 into the femoral head may be too anterior (position D), or too posterior (position E), rather than being in the correct center (position F). Thus, in order to obtain correct placement of the guide pin in the center of the femoral head and neck, the surgeon must perform fine-tuning, trial-and-error adjustment by changing the depth and rotation of the IM nail to vary the position at which the guide pin is inserted and repeatedly drilling with the guide pin 130 under fluoroscopic image intensification until a correct guide-pin position is confirmed by anteroposterior (vertical) and lateral (horizontal) views.

This trial-and-error adjustment increases the length of time a patient has to undergo an operation. It also increases the risk of bleeding, wound contamination and subsequent infection. It also increases the likelihood of bone damage from repeated drilling and potential iatrogenic fractures. This also adds unnecessary radiation exposure to the patient, surgeon, and other operating room personnel.

It should also be noted that inadvertent drilling beyond the articular surface of the femoral head is a problem with the presently available systems.

Also, it is frequently difficult to confirm the position of the guide pin in central axis or near the central axis line of the femoral neck and head because the drill guide and its handle hide the true lateral view of the femoral head and neck even where a radio-lucent drill guide is used.

It is an object of the invention to provide apparatus and methods to overcome the problems discussed above.

SUMMARY OF THE INVENTION

Apparatus and methods embodying the invention include an alignment guide for setting the position and depth of a guide pin to be inserted into a bone. The alignment guide includes means for deploying a guide rod along a selected external surface of a bone, and for adjusting the guide rod so it lies parallel to a desired path extending through the bone and for a selected distance along the length of the bone. The apparatus includes means for subsequently enabling a guide pin to be inserted within the bone along the desired path, parallel to the guide rod. The means for adjusting the guide rod may include imaging means for viewing the location of the desired path extending through (e.g., the center line) the bone and the spatial relationship between the desired path (e.g., the center line) of the bone and the guide rod whereby the apparatus may be used to drill a hole through and along the desired path (e.g., the center) of the bone for a distance also identified by the guide rod. Note that in the discussion to follow the term "guide pin" refers to a pin driven into, or through, a bone producing a path which functions as the axis and guide for a screw or blade to be subsequently inserted into the bone. The term "guide rod" as used herein and in the appended claims refers to a rod positioned externally (over, below or on either side, but not within the bone) to a bone to enable a drill guide to be properly positioned to propel the guide pin in the corresponding bone.

In one embodiment an alignment guide mounted on a drill guide is used to control the position or point at which the guide pin is inserted into the bone and the distance to which guide pin is drilled/inserted into the bone. The alignment guide includes a guide rod which is deployed externally to and along the bone to be drilled (i.e., non-invasively to the bone) and includes adjusting means for positioning the guide rod until it lies parallel to a desired plane running through the bone to be drilled. A drill can then be used to propel a guide pin along a desired (anticipated) path.

One embodiment of the invention is directed to a new alignment guide to aid a surgeon in centering the guide pin to be inserted in the femoral head and neck without repeated trial-and-error drilling. This shortens the operation time and reduces the radiation due to prolonged exposure to fluoroscopic equipment and reduces the risk of possible complications from the surgery.

BRIEF DESCRIPTION OF THE DRAWINGS

In the accompanying drawing like reference characters denote like components.

FIGS. 5A, 5B, 5C, and 5D are various perspective views of an alignment guide embodying the invention;

DETAILED DESCRIPTION OF THE INVENTION

Figure 6A:
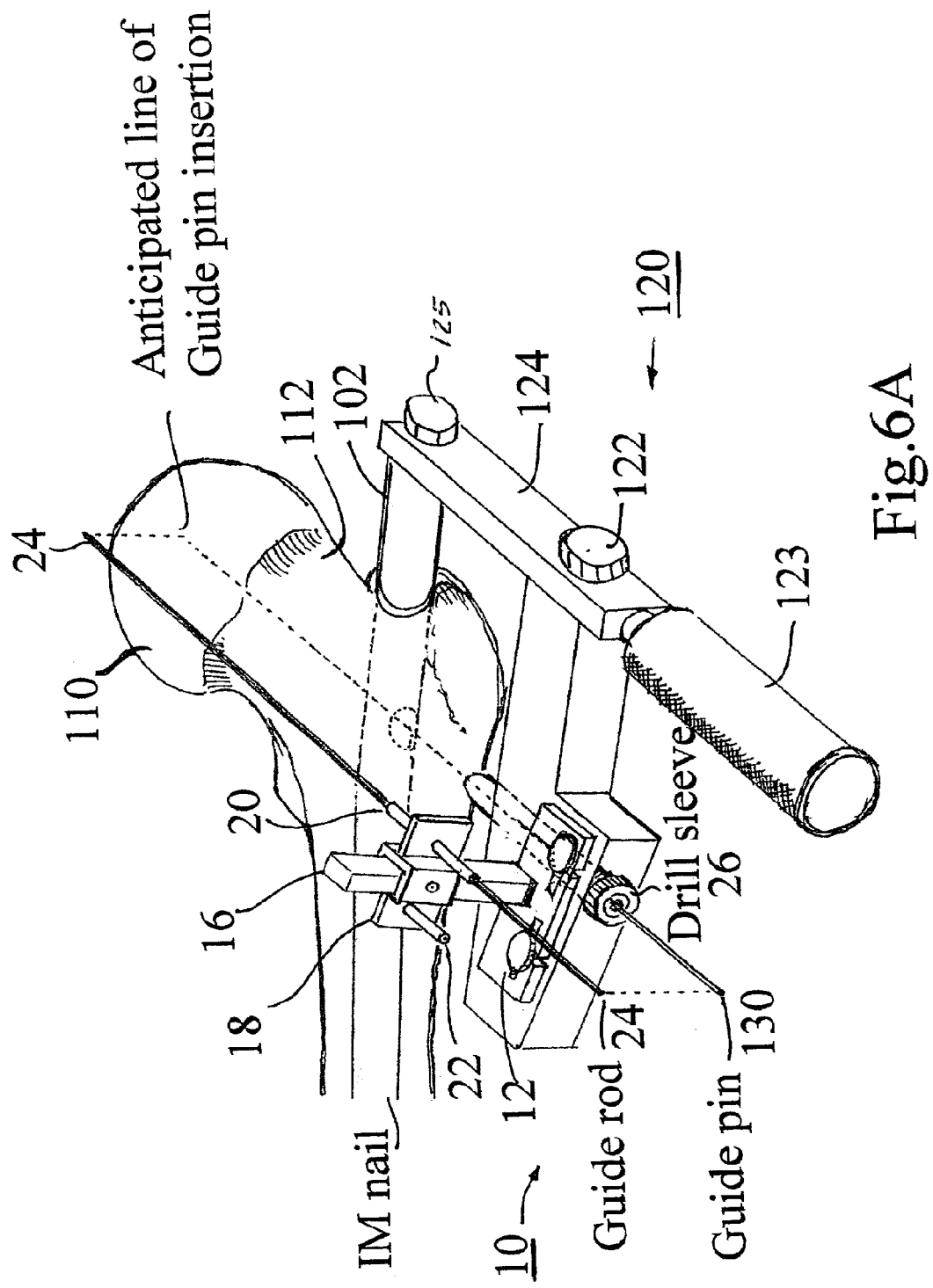
FIG. 6A is a perspective diagram of the alignment guide embodying the invention mounted on the prior art drill guide.
Figure 6B:
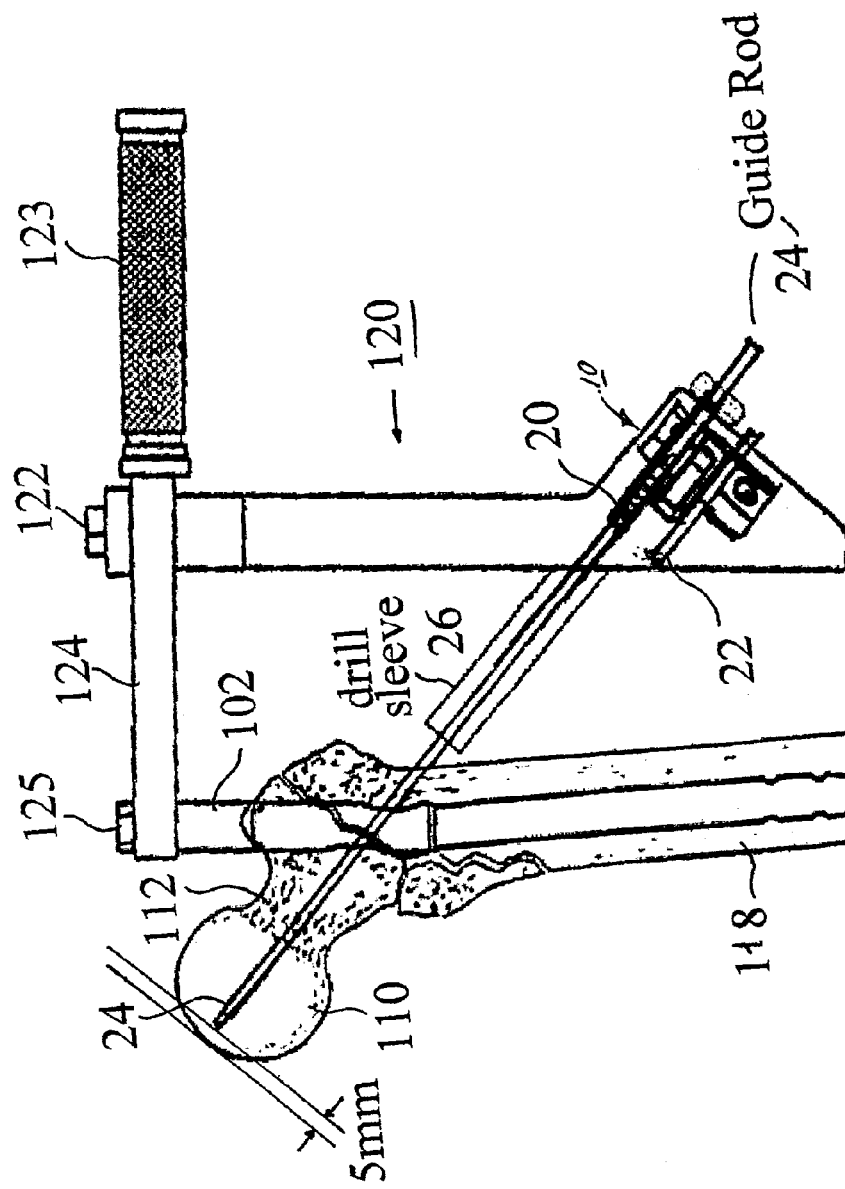
FIG. 6B is a perspective diagram of the alignment guide embodying the invention mounted on the prior art drill guide.
Figure 7:
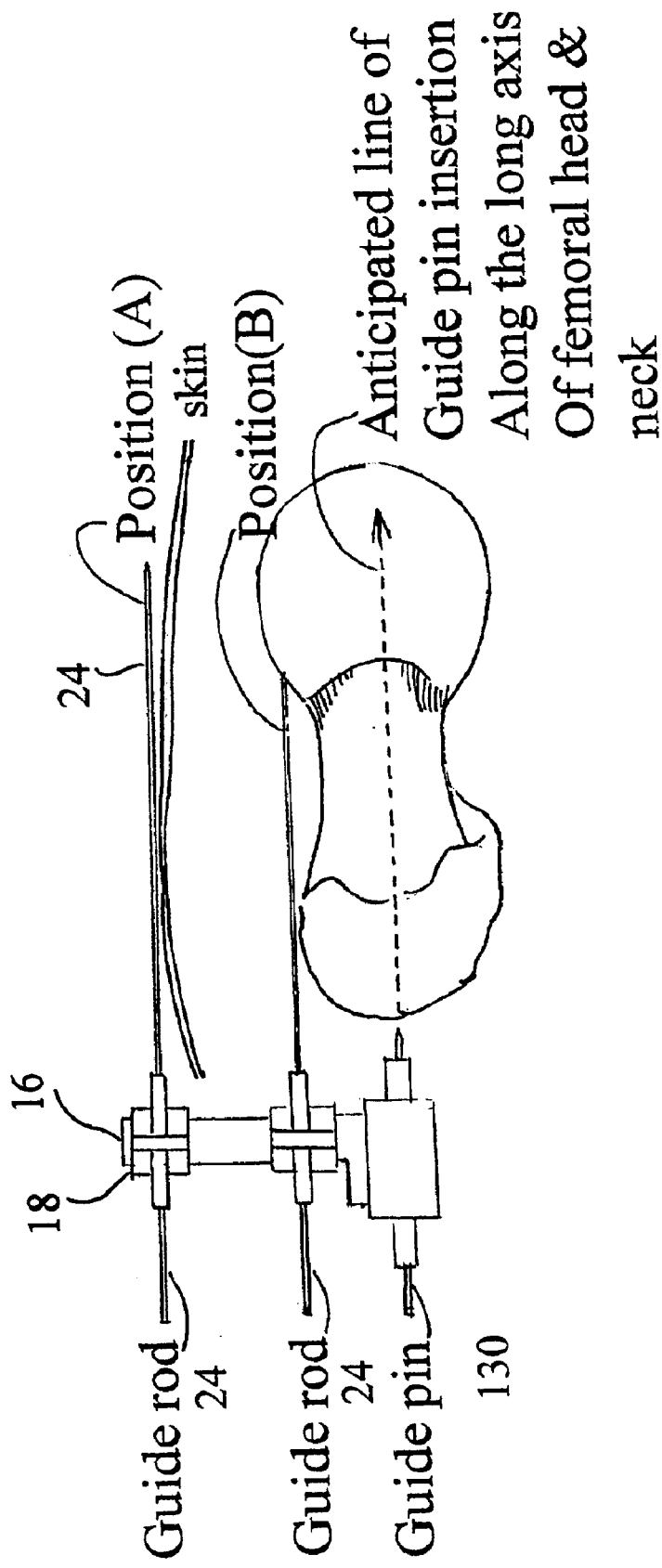
FIG. 7 is a lateral view of a guide rod positioned in accordance with the invention.

FIGS. 5–7 show various aspects of the apparatus embodying the invention. Different views of the alignment guide 10 embodying the invention are shown in FIGS. 5A, 5B, 5C and 5D. The alignment guide 10 is designed to be mounted on a drill guide 120 (see FIGS. 6A, 6B) to help determine the positioning and orientation of the drill guide 120 to ensure that a guide pin 130 is inserted into a selected bone at the appropriate angle (laterally and vertically) and for the desired distance (depth). The alignment guide 10 includes a mechanical assembly for deploying a calibrated guide rod 24 along the surface of a selected bone. The tip of the guide rod 24 may be pointed to enable it to penetrate soft tissue surrounding the selected bone; but the tip of the guide rod is blunt enough to avoid injury to neurovascular structures. The alignment guide 10 is linked to the drill guide 120 so that when the drill guide is used to insert a guide pin into the selected bone, the guide pin is inserted into the selected bone along a path parallel to the guide rod.

The alignment guide 10 includes a base 12 with positioning slots 14a and 14b and a post 16 extending vertically upwards from the base. Base fastening screws 15 may be used to secure the alignment guide 10 to drill guide 120. The base 12 is designed to enable the alignment guide 10 to be attached to an existing drilling guide 120, also denoted as a targeting device, or an aiming arm, and includes means (slots 14a, 14b) for producing fine longitudinal adjustment to obtain correct AP (vertical) alignment between a guide rod 24 and a guide pin 130.

The alignment guide also includes a guide rod holder 18 with two tubes 20 and 22 for holding one or two calibrated guide rods 24. In a single blade or lag screw system (see FIG. 1B or 1C), one of the two guide holder tubes (20, 22) holds one guide rod 24. In a double lag screw system (see FIG. 1A), each one of the two tubes (20, 22) of the guide rod holder 18 holds a guide rod 24. The guide rod holder 18 can be moved up and down post 16 and can be fixed in position via a set screw 181, or any suitable pinning arrangement. As discussed below, moving the guide rod holder 18 enables the guide rod to be moved closer to, or away from, the selected bone in order to image the guide rod and guide pin path within a selected viewing screen and/or to accommodate persons having more or less soft tissue about the selected bone. Thus, the post 16 includes means for vertical height adjustment of the guide rod holder 18 to enable the obtaining of a correct lateral alignment between a guide rod 24 and a guide pin 130 and the long axis of the selected bone (e.g., femoral head and neck).

The tip of the guide rods which extends beyond the guide holder 18 may be positioned to within a given distance (e.g., 5 mm see FIG. 6B) of the articular surface of the femoral head. The guide rod 24 is calibrated to measure the maximum desired distance to the articular surface and to then use that information to set the maximum allowable penetration depth of the guide pin 130 into the femoral head to avoid inadvertent penetration into the hip joint.

FIG. 6A is a perspective diagram showing the alignment guide 10 mounted on the drill guide 120. Note that when the alignment guide 10 is mounted on the guide drill, the guide rod 24 held in tube 20 (or 22) will run parallel to the anticipated line that the guide pin 130 will follow when inserted into the bone. A drill (not shown) is coupled to the guide pin 130 to impel it forward as further discussed below. The handle 123 of the drill guide 120 is connected to an arm 124 which at its distal end is coupled to the IM nail 102 and secured thereto via a screw 125. The drill guide 120, the handle 123 and the arm 124 are secured to each other by means of a screw 122. As already noted, in the apparatus shown in FIGS. 6A and 6B, the guide rod 24 is coupled to the drilling guide 120 such that the anticipated path of the guide pin 130 runs parallel to the path defined by guide rod 24. For the single screw or blade system, using an imaging device to view the femoral head 110 and the neck 112 and the projection of guide rod 24, the drilling device 120 may be moved up and down and rotated until the AP (vertical) view and the lateral view indicate that the anticipated path of guide pin 130, which will be parallel to guide rod 24, would in fact pass through the center of neck region 112 and femoral head 110. Furthermore, by using a calibrated guide rod 24, it is possible to determine how far the guide pin 130 should be inserted into the bone to be within the predetermined distance (e.g., 5 or 10 millimeters) of the articular surface of femoral head 110.

Figure 2:
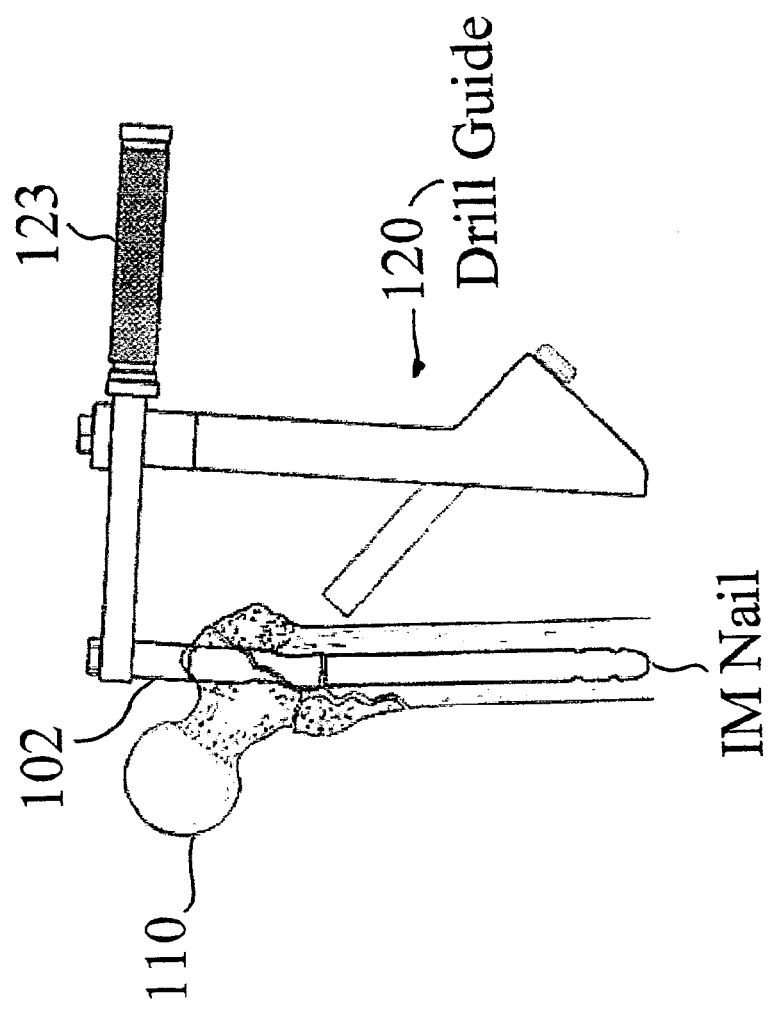
FIG. 2 is a cross sectional diagram of a prior art drill guide coupled to an IM nail.
Figure 3:
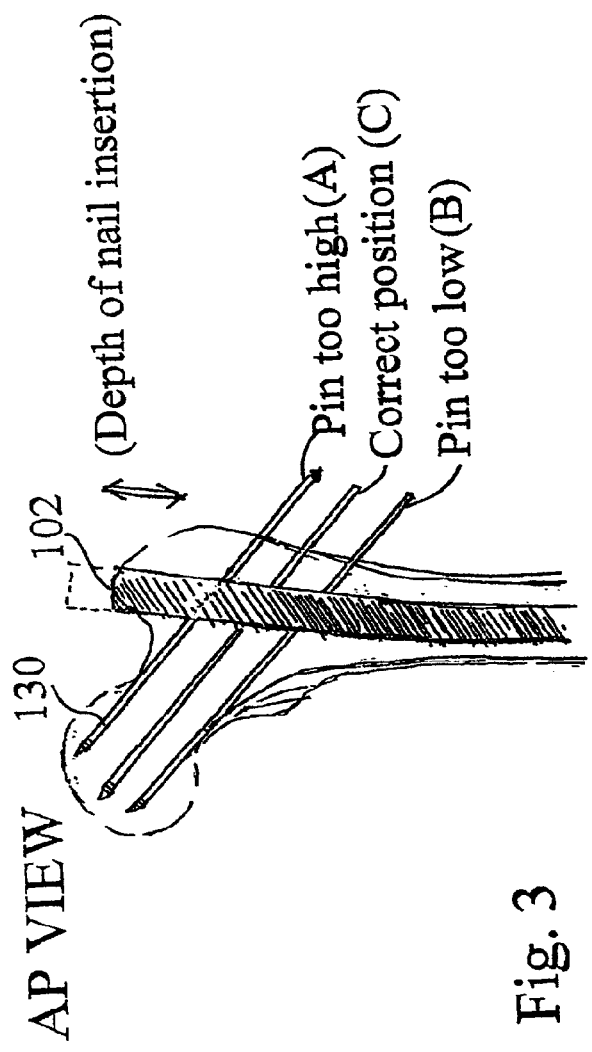
FIG. 3 is a cross sectional anteroposterior (AP) view of a hip bone.

A method for using the alignment guide 10 linked to the drill guide unit 120, as shown in FIGS. 6A and 6B, may be as follows:

1. The medullary canal of the femur 118 is prepared for the insertion therein of an IM nail 102. The IM nail-drill guide unit 120 is assembled and the IM nail 102 may be introduced into the prepared medullary canal of the femur, as shown in FIG. 2.
2. The alignment guide 10 is attached to the drill guide as shown in FIGS. 6A and 6B by use of base fasteners 15 in slots 14a, 14b, as shown in FIGS. 5A and 5D.
3. A calibrated guide rod 24 is inserted into the tube 20 or 22 of guide rod holder 18 mounted on post 16 of base 12 as shown in FIGS. 5C and 5D. Using the base fastener arrangement (slots 14a, 14b and base fasteners 15) of alignment guide 101 fine longitudinal adjustment may be made until the guide rod 24 is aligned with the center line of the drill sleeve 26, or partially inserted guide pin 130, as shown in FIGS. 6A and 6B. The alignment between the guide rod 24 and the guide pin 130 remains fixed during the remainder of the procedure. This is significant since guide pin 130 will then follow an anticipated path through the neck and femoral head bone section which is parallel to the guide rod 24 as deployed along the bone.
4. The length of the guide rod 24 extending over the bone is adjusted to position its tip within, for example, 5 mm of the articular surface of the femoral head as shown in FIGS. 6A and 6B. Using a calibrated guide rod enables the determination of the preferred distance the guide pin has to be inserted within the selected bone.

Figure 1:
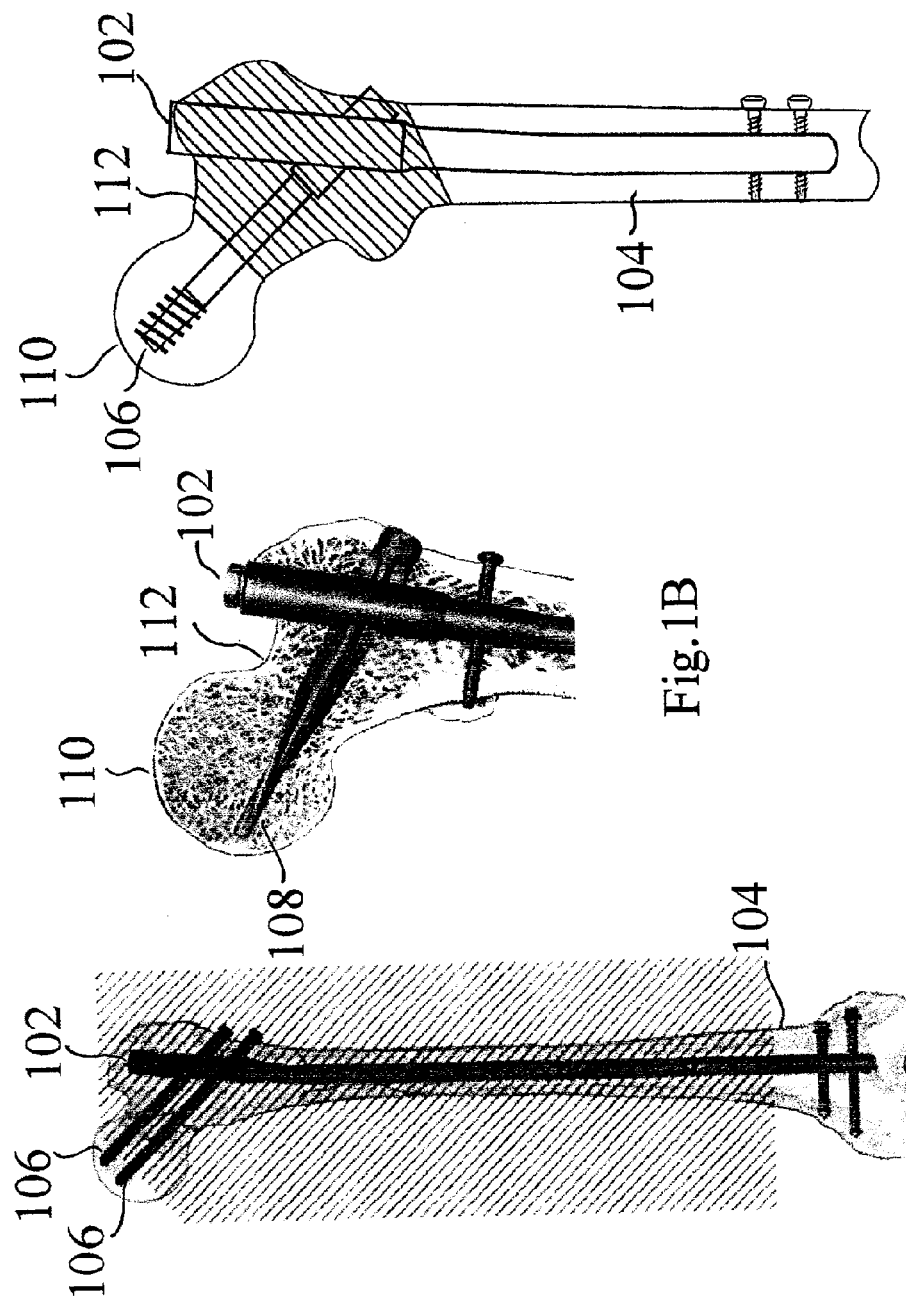
FIGS. 1A, 1B and 1C are cross-sectional diagrams showing an intramedullary nail (IM nail) inserted into the medullary canal of a femur with nails, blades and screws positioned through the IM nail and the femoral neck and head.

5. The IM nail 102 may be raised or lowered or rotated by, for example, applying manual pressure to handle 123 and/or arm 124 and/or tapping on screw 125. For a single screw or blade system (see FIGS. 1B and 1C) the IM nail 102 is slowly advanced under fluoroscopy, or under any similar imaging system, until the guide rod 24 is aligned with the center line of the femoral head 110 and neck 112, as shown in FIGS. 6A and 6B. For a two screw system, as shown in FIG. 1A, two parallel guide rods would be mounted in tubes 20 and 22 to produce the two parallel paths for the guide pins to follow.

Figure 4:
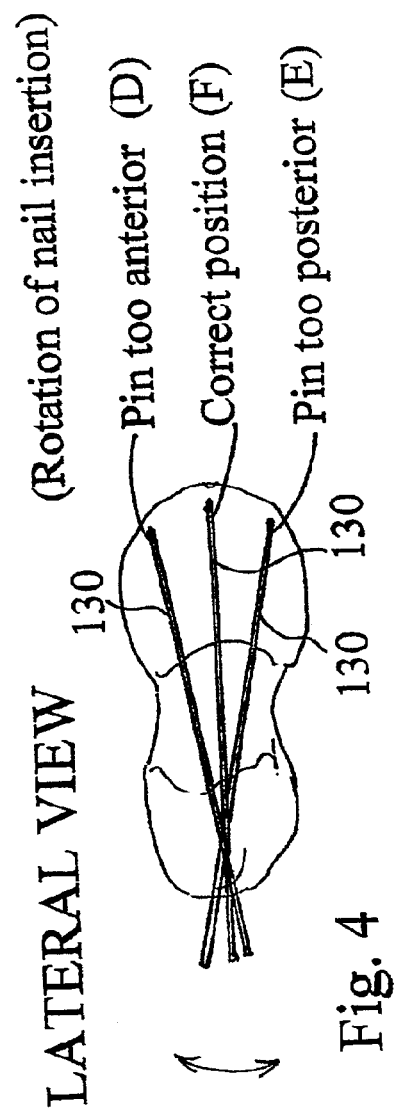
FIG. 4 is a cross sectional lateral view of the femoral neck and head.

6. To achieve lateral (rotational) adjustment, the guide rod holder 18 is lowered along post 16 (see FIGS. 5A, 5D) until the guide rod rests on the skin surface of the anterior aspect of the patient's hip joint as shown for position A in FIG. 7. The lateral (top) view of the femoral head and neck and the guide rod may be displayed on a screen (not shown) which would display an image as shown in FIG. 4. From the lateral display and knowing the projection of the guide rod 24 onto the bone, the anticipated line which the guide pin will take when inserted into the femoral head and neck may be deduced. [Note: If it is not possible to obtain a lateral view of the femoral head and neck and the guide rod in the same screen, the guide rod is withdrawn and reintroduced through the soft tissue along the anterior aspect of the femoral head and neck as shown for position B in FIG. 7, without going into the bone.]

7. The IM nail drill guide 120 with the alignment guide 10 is rotated until the guide rod 24 is parallel to the long axis of the femoral head and neck as shown in FIG. 7.

8. The distance the guide pin 130 is driven into the selected bone is set according to the measurement obtained from the calibrated guide rod.

9. The IM nail drill guide unit 120 with the alignment guide 10 is now positioned to provide correct placement of the guide pin 130 in the center of the femoral head and neck in both the AP (elevation) and lateral (horizontal) planes.

10. A drill attached to the guide pin can then propel the guide pin through the bone along the anticipated path for the desired length. Subsequently, a reamer may be used to increase the size of the hole and a screw or a blade may be superimposed over the guide pin to hold together the trochanter, the neck 112 and the femoral head 110.

The invention has been illustrated by showing how the alignment guide 10 is attached to an existing drill guide 120. However, it should be appreciated that the invention may be practiced using any specially designed piece of equipment incorporating the function of the drill guide 120 and the alignment guide 10. That is, the invention is directed to a guide rod which may be manipulated to lie in a plane parallel to a bone through which a guide pin is to be inserted. The guide rod is coupled to a guide-drill in such a manner that the guide pin, propelled through the bone by a drill (not shown), follows a path through the bone which is parallel to that of the guide rod.

The invention has been illustrated for the case of the hip bone. But it should be appreciated that the invention is suitable to take care of any other bone (e.g., the humerus).

The invention has been illustrated with the path of the guide pin going through the center of a selected bone. But it should be understood that other paths may be selected, as in the case of the two screw system.

What is claimed is:

1. Apparatus for bone fixation comprising:
    a drill guide for inserting a guide pin through a selected bone;
    an alignment guide for holding and deploying a guide rod externally to and along the length of the selected bone in a direction in which the guide pin is to be inserted into the selected bone, said alignment guide including means for: (a) selectively and continuously varying the height of the guide rod relative to the selected bone, and (b) selectively and continuously varying the length of the guide rod extending along the selected bone; and
    means mechanically coupling the drill guide and the alignment guide for causing the guide pin to pass through the selected bone in a direction parallel to the guide rod in all planes defined by the guide rod.

2. Apparatus as claimed in claim 1 wherein at least one of the alignment guide and drill guide and the guide rod are fixedly mounted relative to the selected bone; and including means for imaging and viewing the guide rod and the selected bone through which the guide pin is to be inserted for selectively adjusting the position of the guide rod to set the anticipated path to be followed by the guide pin when subsequently inserted through the selected bone.

3. Apparatus as claimed in claim 1, wherein the alignment guide includes means for selectively and continuously moving the guide rod from side to side in the lateral direction and up and down in the anterior-posterior (AP) direction relative to the selected bone into which the guide pin is to be inserted.

4. Apparatus as claimed in claim 1, wherein the guide rod is calibrated to determine the distance to which the guide pin should extend within the selected bone.

5. Apparatus as claimed in claim 1, wherein the apparatus for bone fixation is for the fixation of a hip bone which includes a femur having a top end from which depends a trochanter, a femoral neck and a femoral head and wherein said drill guide and alignment guide include: (a) means for holding and adjusting an intramedullary (IM) nail inserted along the length of the femur, said IM nail having a preset through hole, (b) a drill sleeve for holding a guide pin and for enabling the guide pin to be urged forward through the trochanter, transversely through the preset through hole in the IM nail, the femoral neck and the femoral head; and (c) means for aligning the guide rod parallel to the path the guide pin is to traverse in both the anterior-posterior (AP) plane and the lateral plane to ensure that the guide pin traverses along a predetermined path at a predetermined angle for a predetermined distance.

6. The apparatus as claimed in claim 5 wherein the drill guide and the alignment guide include means for selectively raising, lowering and rotating the intramedullary (IM) nail until the guide rod is properly positioned for ensuring the subsequent insertion of the guide pin through the preset through hole in the IM nail into the selected bone along a desired path which is parallel to the guide rod in both the anterior-posterior (AP) plane and the lateral plane defined by the guide rod.

7. The apparatus as claimed in claim 6 wherein the preset through hole in the IM nail is cut at a preset angle, and wherein the guide rod is positioned and oriented to ensure that the guide pin is inserted through the preset hole in the IM nail at the preset angle along the center line of the selected bone or along any other desired passageway in the selected bone.

8. The apparatus as claimed in claim 6 wherein the alignment guide includes means for holding two guide rods in parallel to each other.

9. Apparatus for inserting a guide pin into a selected bone includes an alignment guide for controlling the positioning of the guide pin and the depth of the guide pin within the selected bone, the alignment guide including means for deploying a guide rod externally to the selected bone and along the length of the selected bone through which the guide pin is to be inserted, said alignment guide including means for: (a) selectively and continuously varying the elevation of the guide rod relative to the selected bone, and (b) selectively and continuously varying the portion of the guide rod extending along the selected bone; the guide rod being linked to the apparatus for inserting the guide pin for causing the path of the guide pin to run parallel to the guide rod; and imaging means for visualizing the guide rod and the selected bone through which a guide pin is to be inserted for adjusting the guide rod relative to the selected bone to ensure that the guide pin follows a desired anticipated path through the selected bone parallel to that of the guide rod in all planes defined by the guide rod.

10. The apparatus as claimed in claim 9, wherein the apparatus is for the fixation of a hip bone which includes a femur having a top end from which depends a trochanter, a femoral neck and a femoral head and wherein said apparatus includes: (a) means for holding and adjusting, including raising, lowering and rotating, an intramedullary (IM) nail inserted along the length of the femur, said IM nail having a preset slot at one end for enabling a lag screw or blade to pass through; (b) a drill sleeve for holding a guide pin and also includes means for propelling the guide pin through the trochanter, through the preset slot of the IM nail and through the femoral neck and the femoral head, and wherein the means for deploying the guide rod includes means for adjusting the height of the guide rod and means for adjusting the lateral placement of the guide rod relative to the selected bone and wherein the guide pin follows a path parallel to that of the guide rod in both the anterior-posterior (AP) plane and the lateral plane when the guide pin passes through the trochanter, the preset slot in the IM nail, the femoral neck and head.

11. The apparatus as claimed in claim 10 including a drill guide and wherein the guide pin is inserted into the bone via the drill guide and wherein the alignment guide is mechanically linked to the drill guide whereby the guide pin follows a path parallel to the path of the guide rod in both the anterior-posterior (AP) plane and the lateral plane.

12. Apparatus as claimed in claim 10, wherein the apparatus for inserting a guide pin into a selected bone includes a drill guide for inserting the guide pin through the IM nail and through the center of the femoral head and neck along a path parallel to the one defined by the guide rod in both the anterior-posterior (AP) plane and the lateral plane defined by the guide rod to ensure that one of the lag screw and blade is correctly positioned when subsequently inserted.

13. A method for bone fixation comprising the steps of:
employing apparatus for deploying a guide rod along the external surface of a selected bone through which a guide pin is to be inserted, the apparatus enabling (a) the elevation of the guide rod relative to the selected bone to be selectively and continuously adjusted (b) the length of the guide rod extending along the length of the bone to be selectively and continuously adjusted, (c) the side to side motion of the guide rod relative to the selected bone to be selectively and continuously adjusted; and (d) controlling the passage of the guide pin along a path parallel to the guide rod in both the vertical and horizontal planes;

displaying the spatial relationship between the guide rod and the selected bone on an imaging and viewing device; and adjusting the guide rod so it defines a desired path within the selected bone through which the guide pin is to be inserted into the selected bone along a path parallel to the one defined by the guide rod in all planes defined by the guide rod.

14. The method of bone fixation as claimed in claim 13 wherein the apparatus is for the fixation of a hip bone which includes the proximal end of the femur from which depends the trochanter, the femoral neck and the femoral head and wherein said apparatus includes means for holding and adjusting an intramedullary (IM) nail, having a preset slot, which is inserted along the length of the femur and also includes a drill sleeve for holding a guide pin and also includes means for propelling the guide pin through the trochanter, through the preset slot of the IM nail and through the femoral neck and femoral head, and further including the step of inserting the guide pin into the selected bone along the desired path parallel to the guide rod in both the anterior-posterior (AP) plane and the lateral plane defined by the guide rod.

15. The method as claimed in claim 14, wherein the guide rod is deployed by means of an alignment guide which includes means for adjusting the height and lateral position of the guide rod.

16. The method as claimed in claim 15 wherein the step of inserting the guide pin includes using a drill guide mechanically linked to the alignment guide for maintaining the guide pin parallel to the path defined by the guide rod in both the anterior-posterior (AP) plane and the lateral plane defined by the guide rod.

17. The method as claimed in claim 16 wherein the selected bone through which the guide pin is to be inserted include the trochanter, the femoral neck and the femoral head.

* * * * *